(12) United States Patent
Lim et al.

(10) Patent No.: US 10,471,431 B2
(45) Date of Patent: Nov. 12, 2019

(54) APPARATUSES, SYSTEMS AND METHODS FOR PROVIDING SCALABLE THERMAL CYCLERS AND ISOLATING THERMOELECTRIC DEVICES

(71) Applicant: LIFE TECHNOLOGIES CORPORATION, Carlsbad, CA (US)

(72) Inventors: Chee Kiong Lim, Singapore (SG); Way Xuang Lee, Singapore (SG); Wuh Ken Loh, Singapore (SG); Chee Wee Ching, Johor Bahru (MY); Chin Yong Koo, Singapore (SG); Siew Ying Koh, Singapore (SG); Tiong Han Toh, Singapore (SG); Kuan Moon Boo, Singapore (SG); Soo Yong Lau, Singapore (SG)

(73) Assignee: LIFE TECHNOLOGIES CORPORATION, Carlsbad, CA (US)

( * ) Notice: Subject to any disclaimer, the term of this patent is extended or adjusted under 35 U.S.C. 154(b) by 96 days.

(21) Appl. No.: 14/613,496

(22) Filed: Feb. 4, 2015

(65) Prior Publication Data
US 2015/0231636 A1    Aug. 20, 2015

Related U.S. Application Data

(60) Provisional application No. 61/940,981, filed on Feb. 18, 2014.

(51) Int. Cl.
*B01L 7/00* (2006.01)
*C12Q 1/6806* (2018.01)

(52) U.S. Cl.
CPC .............. *B01L 7/52* (2013.01); *C12Q 1/6806* (2013.01); *B01L 2200/147* (2013.01);
(Continued)

(58) Field of Classification Search
CPC .......................... B01L 2300/1822; B01L 7/52
See application file for complete search history.

(56) References Cited

U.S. PATENT DOCUMENTS 3,036,893 A    5/1962  Natelson
3,128,239 A    4/1964  Page
(Continued)

FOREIGN PATENT DOCUMENTS

CN    102892508    1/2013
CN    103003448    3/2013
(Continued)

OTHER PUBLICATIONS

PCT/US2015/014357, International Search Report and Written Opinion dated Apr. 29, 2015, 15 Pages.
(Continued)

*Primary Examiner* — Jonathan M Hurst
(74) *Attorney, Agent, or Firm* — Jones Robb, PLLC

(57) ABSTRACT

In one aspect, a thermal cycler system including a sample block and a thermoelectric device is disclosed. In various embodiments, the sample block has a first surface configured to receive a plurality of reaction vessels and an opposing second surface. In various embodiments the thermoelectric device is operably coupled to the second surface of the sample block. In various embodiments a thermal control unit is provided. In various embodiments the thermal control unit includes a computer processing unit. In various embodiments the thermal control unit includes an electrical current source. In various embodiments the thermal control unit also includes an electrical interface portion configured to connect the thermoelectric device with the electrical current source by way of an electrical cable. In various embodiments the thermal control unit is oriented in a different plane than the sample block and thermoelectric cooler.

29 Claims, 8 Drawing Sheets

(52) U.S. Cl.
CPC .......... B01L 2300/0829 (2013.01); B01L 2300/1805 (2013.01); B01L 2300/1822 (2013.01); B01L 2300/1883 (2013.01)

(56) References Cited

U.S. PATENT DOCUMENTS

| | | |
|---|---|---|
| 3,216,804 A | 11/1965 | Natelson |
| 3,260,413 A | 7/1966 | Natelson |
| 3,261,668 A | 7/1966 | Natelson |
| 3,271,112 A | 9/1966 | Williams et al. |
| 3,331,665 A | 7/1967 | Natelson |
| 3,368,872 A | 2/1968 | Natelson |
| 3,556,731 A | 1/1971 | Martin |
| 4,865,986 A | 9/1989 | Coy et al. |
| 4,950,608 A | 8/1990 | Kishimoto et al. |
| 5,038,852 A | 8/1991 | Johnson et al. |
| 5,061,630 A | 10/1991 | Knopf et al. |
| 5,224,536 A | 7/1993 | Eigen et al. |
| 5,333,675 A | 8/1994 | Mullis et al. |
| 5,430,957 A | 7/1995 | Eigen et al. |
| 5,441,576 A | 8/1995 | Bierschenk et al. |
| 5,475,610 A | 12/1995 | Atwood et al. |
| 5,504,007 A | 4/1996 | Haynes |
| 5,525,300 A | 6/1996 | Danssaert et al. |
| 5,601,141 A | 2/1997 | Gordon et al. |
| 5,602,756 A | 2/1997 | Atwood |
| 5,656,493 A | 8/1997 | Mullis et al. |
| 5,716,842 A | 2/1998 | Baier et al. |
| 5,802,856 A | 9/1998 | Schaper et al. |
| 5,819,842 A | 10/1998 | Potter et al. |
| 5,871,908 A | 2/1999 | Henco et al. |
| 6,015,534 A | 1/2000 | Atwood |
| 6,093,370 A | 7/2000 | Yasuda et al. |
| 6,106,784 A | 8/2000 | Lund et al. |
| 6,337,435 B1 | 1/2002 | Chu et al. |
| 6,525,550 B2 | 2/2003 | Pan |
| 6,558,947 B1 | 5/2003 | Lund et al. |
| 6,633,785 B1 | 10/2003 | Kasahara et al. |
| 6,767,512 B1 | 7/2004 | Lurz et al. |
| 6,814,934 B1 | 11/2004 | Higuchi et al. |
| 6,825,047 B1 | 11/2004 | Woudenberg et al. |
| 7,611,674 B2 | 11/2009 | Heimberg et al. |
| 7,727,479 B2 | 6/2010 | Wolfgang et al. |
| 8,389,288 B2 | 3/2013 | Heimberg et al. |
| 8,676,383 B2 | 3/2014 | Tan et al. |
| 8,721,972 B2 | 5/2014 | Heimberg et al. |
| 9,457,351 B2 | 10/2016 | Tan et al. |
| 9,566,583 B2 | 2/2017 | Conner et al. |
| 2001/0001644 A1 | 5/2001 | Coffman et al. |
| 2002/0001848 A1 | 1/2002 | Bedingham et al. |
| 2002/0068357 A1 | 6/2002 | Mathies et al. |
| 2003/0214994 A1 | 11/2003 | Schicke et al. |
| 2004/0065655 A1* | 4/2004 | Brown .............. B01L 3/50851 219/428 |
| 2004/0076996 A1 | 4/2004 | Kondo et al. |
| 2004/0122559 A1 | 6/2004 | Young et al. |
| 2004/0241048 A1 | 12/2004 | Shin et al. |
| 2005/0133724 A1 | 6/2005 | Hsieh |
| 2005/0247357 A1 | 11/2005 | Welle |
| 2006/0001644 A1 | 1/2006 | Arakawa et al. |
| 2006/0024816 A1 | 2/2006 | Fawcett et al. |
| 2006/0228268 A1 | 10/2006 | Heimberg et al. |
| 2007/0054568 A1* | 3/2007 | Roset .............. H01R 4/20 439/877 |
| 2008/0026483 A1 | 1/2008 | Oldenburg |
| 2008/0087316 A1 | 4/2008 | Inaba et al. |
| 2008/0176292 A1 | 7/2008 | Ugaz et al. |
| 2008/0274511 A1 | 11/2008 | Tan et al. |
| 2009/0155765 A1 | 6/2009 | Atwood et al. |
| 2009/0325277 A1 | 12/2009 | Shigeura et al. |
| 2010/0081191 A1* | 4/2010 | Woods .............. B01L 7/52 435/303.1 |
| 2010/0116896 A1 | 5/2010 | Goemann-Thoss et al. |
| 2010/0120099 A1 | 5/2010 | Heimberg et al. |
| 2010/0120100 A1 | 5/2010 | Heimberg et al. |
| 2010/0124766 A1* | 5/2010 | Ng .............. B01L 7/52 435/91.2 |
| 2010/0165784 A1 | 7/2010 | Jovanovich et al. |
| 2011/0275055 A1* | 11/2011 | Conner .............. B01L 7/52 435/3 |
| 2013/0157376 A1 | 6/2013 | Nay |

FOREIGN PATENT DOCUMENTS

| | | |
|---|---|---|
| CN | 102483642 A | 12/2014 |
| DE | 1900279 | 9/1969 |
| DE | 19646115 A1 | 5/1998 |
| DE | 102007003754 | 7/2008 |
| EP | 0089383 A1 | 9/1983 |
| EP | 0488769 A2 | 6/1992 |
| EP | 0545736 A2 | 6/1993 |
| EP | 0776967 A2 | 6/1997 |
| EP | 0812621 A1 | 12/1997 |
| JP | 2000-102376 | 4/2000 |
| JP | 2001-275652 | 10/2001 |
| JP | 2010502228 | 1/2010 |
| JP | 2012-170337 | 9/2012 |
| RU | 2106007 | 2/1998 |
| WO | WO-1989/012502 A1 | 12/1989 |
| WO | WO-1990/005947 A1 | 5/1990 |
| WO | WO-1992/004979 A1 | 4/1992 |
| WO | WO-1995/011294 A1 | 4/1995 |
| WO | WO-1998/020975 A1 | 5/1998 |
| WO | WO-1998/043740 | 10/1998 |
| WO | WO-1999/016549 | 4/1999 |
| WO | WO-2001/024930 | 4/2001 |
| WO | 2004/108288 | 12/2004 |
| WO | WO-2004/105947 | 12/2004 |
| WO | WO-2007/146443 | 12/2007 |
| WO | WO-2008/030914 | 3/2008 |
| WO | WO-2008/070198 | 6/2008 |
| WO | 2008/116184 | 9/2008 |
| WO | WO-2009/094061 | 7/2009 |
| WO | WO-2010012494 A1 | 2/2010 |
| WO | 2011/124918 | 10/2011 |
| WO | WO-2011127386 A2 | 10/2011 |
| WO | WO-2012/073484 | 6/2012 |
| WO | WO-2012/080746 | 6/2012 |
| WO | WO-2013133725 A1 | 9/2013 |
| WO | WO-2015039014 A1 | 3/2015 |

OTHER PUBLICATIONS

"Cooling Machine CPU Cooler, Thermaltake,", printed from http://ww.thermaltake.com/coolers/4in1_heatpipe/cl-pO114bigtyphoon/cl-pO114.htm, May 8, 2006, 1-2.

"CoolerMaster Expand Your Imagination, Hyper 6 (KHC-V81)", printed from http://www.coolermaster.com/index.php?LT=english&Language_s=2&url_place=product&pserial=KHC-V81&oth, May 8, 2006, 1-5.

"LightCycler® 480 System Rapid by Nature—Accurate by Design", *Roche Diagnostics*, printed from www.roche-applied-science.com, Nov. 3, 2009, 1-16.

"Stratagene", *Quantitative PCR Systems*, May 2006, 1-12.

Cheng, J.Y., et al., "Performing Microchannel Temperature Cycling Reactions Using Reciprocating Reagent Shuttling Along a Radial Temperature Gradient", 2005, 931-940.

EP11766806.1, "Extended European Search Report for Application No. 11766806.1 dated Nov. 5, 2013", Nov. 5, 2013, 1-5.

PCT/US2011/031750, "International Preliminary Examination Report on Patentability dated Aug. 23, 2016", Aug. 23, 2016, 1-11.

EP3107658B1, "Communication of Notice of Opposition", dated Apr. 4, 2019, English translation, 29 pages.

EP3107658B1, "Communication of Notice of Opposition", dated Apr. 4, 2019, German language, 32 pages.

Extended European Search Report for Application No. 18180197.8, dated Aug. 2, 2018, 4 pages.

* cited by examiner

APPARATUSES, SYSTEMS AND METHODS FOR PROVIDING SCALABLE THERMAL CYCLERS AND ISOLATING THERMOELECTRIC DEVICES

CROSS-REFERENCE TO RELATED APPLICATIONS

This application claims priority to U.S. application No. 61/940,981 filed Feb. 18, 2014, which disclosure is herein incorporated by reference in its entirety.

FIELD

The present disclosure generally relates to apparatuses, systems and methods for providing scalable thermal cycler and isolating thermoelectric devices.

BACKGROUND

Thermal cycling in support of Polymerase Chain Reaction (PCR) is a ubiquitous technology found in over 90% of molecular biology laboratories worldwide.

Amplifying DNA (Deoxyribose Nucleic Acid) using the PCR process, involves cycling a specially constituted liquid reaction mixture through several different temperature incubation periods. The reaction mixture is comprised of various components including the DNA to be amplified and at least two primers sufficiently complementary to the sample DNA to be able to create extension products of the DNA being amplified. A key to PCR is the concept of thermal cycling: alternating steps of denaturing DNA, annealing short primers to the resulting single strands, and extending those primers to make new copies of double-stranded DNA. In thermal cycling the PCR reaction mixture is repeatedly cycled from high temperatures of around 95° C. for denaturing the DNA, to lower temperatures of approximately 50° C. to 70° C. for primer annealing and extension.

In some previous PCR instruments, sample tubes are inserted into sample wells on a metal block. To perform the PCR process, the temperature of the metal block is cycled according to prescribed temperatures and times specified by the user in a PCR protocol. The cycling is controlled by a computer and associated electronics. As the metal block changes temperature, the samples in the various tubes experience similar temperature changes. However, in these previous instruments the overall size or footprint is frequently large and therefore occupy significant space on a laboratory bench. In many laboratories open bench space is frequently hard to find. In some previous instruments a reason for the relatively large footprint can be due to the dimensions of the various components and subassemblies required to cycle samples to perform the PCR process.

Components that contribute to the overall size of the instrument are the printed circuit boards (PCBs) used to provide the thermal control of the metal block and ultimately of the sample. In some previous instruments two printed circuit boards are included. One of the PCBs sometimes referred to as an Interface Board, is positioned around the perimeter of the thermoelectric devices and can be used to provide electrical connections to the thermoelectric devices, thermal sensors and other necessary electronics. Another PCB, sometimes referred to as an Amplifier Board, can be used to provide electrical currents to the thermoelectric devices in a controlled manner dependent on the desired or setpoint temperature of the metal block and the temperature of the metal block or sample detected by a thermal sensor.

Thermoelectric devices utilize the Peltier effect to pump heat from one side of the device to another. In operation, a thermoelectric device is provided with an electrical DC current. Current flows through the TEC and results in one surface becoming hot while the opposing surface becomes cold. By reversing the direction of the current the surface that was hot becomes cold and the surface that was cold becomes hot.

Frequently thermoelectric devices do not perform well in environments that are moist. Moisture contributes to corrosion of electrical connections within the device. The corrosion increases the resistance of the connections and eventually results in a premature failure of the device, and low reliability of the instrument.

In some previous instruments the number of thermoelectric devices and the size of each thermoelectric device can be large. In some previous instruments the number of thermoelectric devices can be 1, 2, 4, 6, 8 or any other number suitable for the application. An Interface Board providing the necessary electrical connections, therefore, can be substantial. Additionally the PCB can be positioned around the perimeter of the TECs, further contributing to the overall size of the instrument.

In some previous instruments thermoelectric devices require significant electrical current to power the thermoelectric devices. Depending on the instrument, the required current may be greater than 10 amperes. Providing currents of this magnitude frequently require the use of large electrical components, for example inductors, to provide the necessary current. The size of the electrical components impacts the size of the Amplifier Board and further impacts the size of the instrument.

Providing small, scalable, reliable and affordable high performance instruments with a small footprint therefore, becomes desirable to scientists around the world.

SUMMARY

Apparatuses, systems and methods for providing scalable thermal cycler and isolating thermoelectric devices are disclosed.

In one aspect, a thermal cycler system includes a sample block and a thermoelectric device is disclosed. In various embodiments, the sample block has a first surface configured to receive a plurality of reaction vessels and an opposing second surface. In various embodiments the thermoelectric device is operably coupled to the second surface of the sample block. In various embodiments a thermal control unit is provided. In various embodiments the thermal control unit includes a computer processing unit. In various embodiments the thermal control unit includes an electrical current source. In various embodiments the thermal control unit also includes an electrical interface portion configured to connect the thermoelectric device with the electrical current source by way of an electrical cable. In various embodiments the thermal control unit is oriented in a different plane than the sample block and thermoelectric cooler.

In another aspect, a thermal cycler system includes a sample block and two or more thermal modules is disclosed. In various embodiments, the sample block has a first surface configured to receive a plurality of reaction vessels and an opposing second surface. In various embodiments, each thermal module includes a thermoelectric device. In various embodiments, the thermoelectric device is operably coupled to the second surface of the sample block. In various embodiments, each thermal module includes a computer processing unit. In various embodiments the thermal control unit includes an electrical current source. In various embodiments the thermal control unit also includes an electrical interface configured to connect the thermoelectric device to the electrical current source by way of an electrical cable. In various embodiments, the thermal control unit is oriented in a different plane than the sample block and thermoelectric cooler.

In another aspect, a thermal cycler apparatus includes a sample block, a thermoelectric device, a drip pan, a heat sink and an opening defined in the heat sink is disclosed. In various embodiments, the sample block has a first surface configured for receiving a sample support device and an opposing second surface. In various embodiments the thermoelectric device is positioned in thermal contact with the second surface of the sample block. In various embodiments, the drip pan surrounds the perimeter of the sample block. In various embodiments, the heat sink is located in thermal contact with the thermoelectric device. In various embodiments, the heat sink and the drip pan are hermetically sealed. In various embodiments, an insert is located in the opening defined in the heat sink. In various embodiments, the insert hermetically seals an electrical connection leading from the thermoelectric device.

In another aspect, a thermal cycling device includes a sample block, a thermoelectric device, a drip pan, a heat sink, an opening defined in the heat sink, a first seal and a second seal is disclosed. In various embodiments, the sample block has a first surface configured to receive a sample support device and an opposing second surface. In various embodiments the thermoelectric device is positioned in thermal contact with the second surface of the sample block. In various embodiments, the drip pan surrounds the perimeter of the sample block and has a top surface and a bottom surface. In various embodiments, the heat sink is located in thermal contact with the thermoelectric device. In various embodiments, the heat sink further comprises a base having a first surface, a second surface, and a plurality of fins pendant the second surface. In various embodiments, the first seal defines the perimeter of the thermoelectric device. In various embodiments, the first seal further isolates the first surface of the heat sink and is configured to provide a hermetic seal with the bottom surface of the drip pan. In various embodiments, the second seal isolates the perimeter of the first surface of the sample block. In various embodiments, the second seal further is configured to provide a hermetic seal with the bottom surface of the drip pan.

In another aspect, a thermal cycling apparatus includes a sample block, a thermoelectric device, a drip pan, a heat sink, a first seal, a second seal, a third seal, and a fourth seal. In various embodiments, the sample block has a first surface and a second surface. In various embodiments, the second surface is configured for receiving a sample support device. In various embodiments, the thermoelectric device is positioned in thermal contact with the second surface of the sample block. In various embodiments, the drip pan surrounds the perimeter of the sample block and has a top surface and a bottom surface. In various embodiments, the heat sink is positioned in thermal contact with the thermoelectric device and comprises a base having a first surface, a second surface, a plurality of fins pendant the second surface, and an opening in the heat sink. In various embodiments, the first seal defines the perimeter of the thermoelectric device. In various embodiments, the first seal further isolates the first surface of the heat sink and is configured to provide a hermetic seal with the button surface of the drip pan. In various embodiments, the second seal isolates the perimeter of the first surface of the sample block. In various embodiments, the second seal if configured to provide a hermetic seal with the bottom surface of the drip pan. In various embodiments, the third seal is located in the defined opening of the heat sink. In various embodiments, the third seal is configured to hermetically seal an electrical connection leading from the thermoelectric device. In various embodiments, the fourth seal is located at the end of the one or more electrical leads attached to the thermoelectric device.

In another aspect, a thermal cycling apparatus includes a sample block, a thermoelectric device, a drip pan, a heat sink, and a plurality of sealing members. In various embodiments, the sample block has a first surface and a second surface. In various embodiments, the first surface is configured for receiving a sample support device. In various embodiments, the thermoelectric device is positioned in thermal contact with the second surface of the sample block. In various embodiments, the drip plan surrounds the perimeter of the sample block. In various embodiments, the drip plan has a top surface and a bottom surface. In various embodiments, the heat sink is positioned in thermal contact with the thermoelectric device and comprises a base having a first surface, a second surface, a plurality of fins pendant the second surface, and an opening defined in the heat sink. In various embodiments, the plurality of sealing members are configured to hermetically seal the thermoelectric device between the sample block and the heat sink.

In another aspect, a method for controlling thermoelectric devices comprises providing an apparatus capable of analyzing biological samples that comprises one or more thermal blocks, one or more thermoelectric devices, and one or more thermal control units, locating each of the thermal control units away from the thermoelectric devices, electronically connecting a unique thermal control unit to one of the thermoelectric devices, and controlling the temperature of each of the thermoelectric devices. In various embodiments, the one or more thermal blocks each have a first surface and a second surface. In various embodiments, the first surface is configured for receiving a sample support device. In various embodiments, the one or more thermoelectric devices are operably coupled to the second surface of at least one thermal block. In various embodiments, the one or more thermal control units are configured to control a single thermoelectric device. In various embodiments, electrically connecting the unique thermal control units to one of the thermoelectric devices is done by way of an electrical cable. In various embodiments, controlling the temperature of each of the thermoelectric devices is done with the unique thermal control units.

These and other features are provided herein.

BRIEF DESCRIPTION OF THE DRAWINGS

For a more complete understanding of the principles disclosed herein, and the advantages thereof, reference is now made to the following descriptions taken in conjunction with the accompanying drawings, in which.

DESCRIPTION OF VARIOUS EMBODIMENTS

Figure 1:
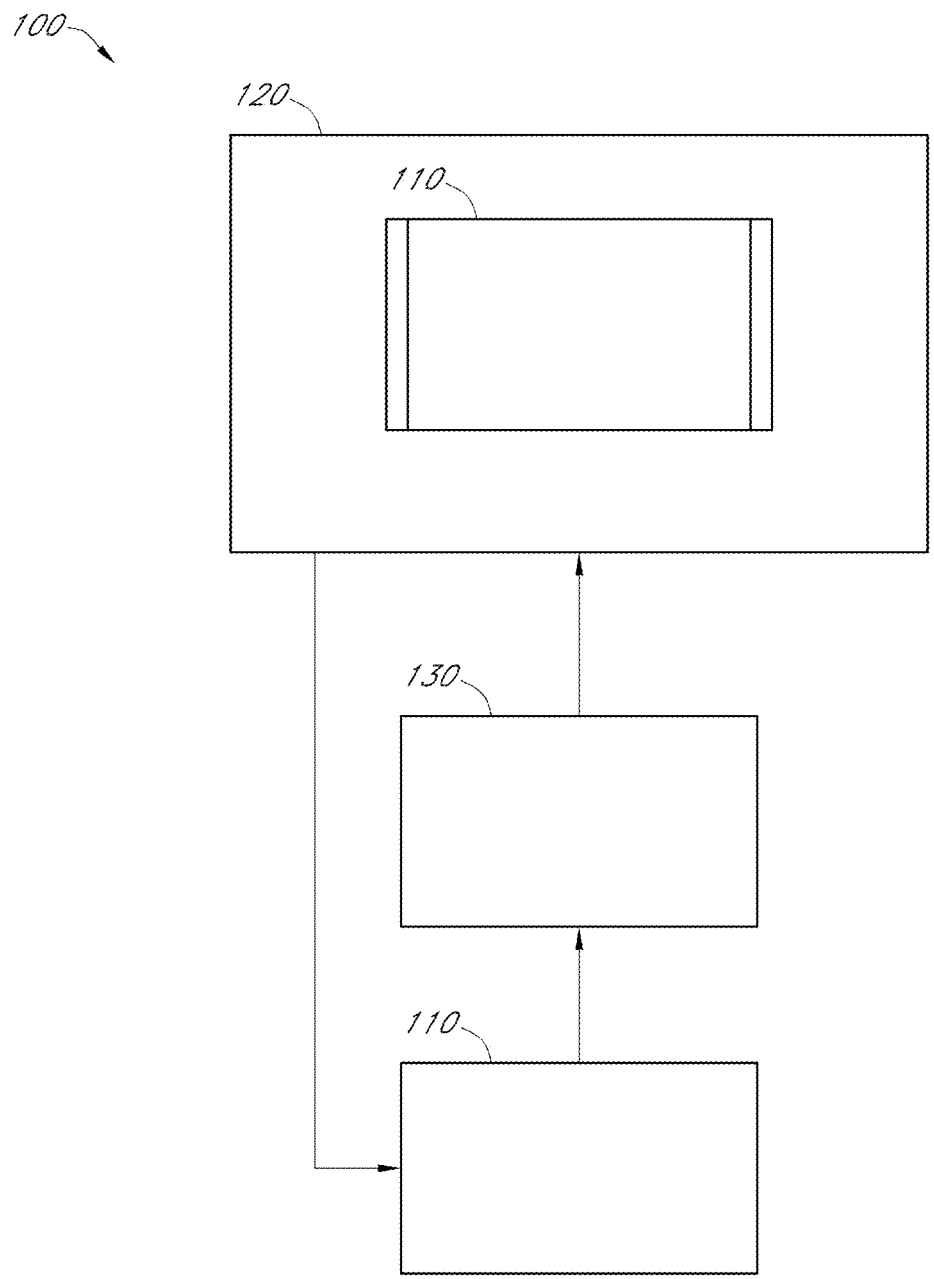
FIG. 1 is a block diagram that illustrates a sample block assembly according to the prior art.

Embodiments of apparatuses, systems and methods for providing scalable thermal cycler and isolating thermoelectric devices are described in this specification. The section headings used herein are for organizational purposes only and are not to be construed as limiting the described subject matter in any way.

Reference will be made in detail to the various aspects of the disclosure, examples of which are illustrated in the accompanying drawings. Wherever possible, the same reference numbers will be used throughout the drawings to refer to the same or like parts.

In this detailed description of the various embodiments, for purposes of explanation, numerous specific details are set forth to provide a thorough understanding of the embodiments disclosed. One skilled in the art will appreciate, however, that these various embodiments may be practiced with or without these specific details. In other instances, structures and devices are shown in block diagram form. Furthermore, one skilled in the art can readily appreciate that the specific sequences in which methods are presented and performed are illustrative and it is contemplated that the sequences can be varied and still remain within the spirit and scope of the various embodiments disclosed herein.

Unless defined otherwise, all technical and scientific terms used herein have the same meaning as is commonly understood by one of ordinary skill in the art to which the various embodiments described herein belongs. When definitions of terms in incorporated references appear to differ from the definitions provided in the present teachings, the definition provided in the present teachings shall control.

It will be appreciated that there is an implied "about" prior to the temperatures, concentrations, times, etc. discussed in the present teachings, such that slight and insubstantial deviations are within the scope of the present teachings. In this application, the use of the singular includes the plural unless specifically stated otherwise. Also, the use of "comprise", "comprises", "comprising", "contain", "contains", "containing", "include", "includes", and "including" are not intended to be limiting. It is to be understood that both the foregoing general description and the following detailed description are exemplary and explanatory only and are not restrictive of the present teachings.

While the present teachings are described in conjunction with various embodiments, it is not intended that the present teachings be limited to such embodiments. On the contrary, the present teachings encompass various alternatives, modifications, and equivalents, as will be appreciated by those of skill in the art.

Further, in describing various embodiments, the specification may have presented a method and/or process as a particular sequence of steps. However, to the extent that the method or process does not rely on the particular order of steps set forth herein, the method or process should not be limited to the particular sequence of steps described. As one of ordinary skill in the art would appreciate, other sequences of steps may be possible. Therefore, the particular order of the steps set forth in the specification should not be construed as limitations on the claims. In addition, the claims directed to the method and/or process should not be limited to the performance of their steps in the order written, and one skilled in the art can readily appreciate that the sequences may be varied and still remain within the spirit and scope of the various embodiments.

Generally, in the case of providing instruments to biological laboratories a smaller physical size of an instrument is beneficial for at least the following reasons. First, in smaller laboratories a smaller instrument can be integrated easier due to limited available workspace. Second, a smaller physical size of an instrument can enable scientists to acquire multiple instruments where previously the workspace may have only accommodated one.

An instrument architecture consistent with the prior art is shown in FIG. 1. Instrument 100 includes thermal block 110, interface board 120, amplifier 130 and main controller board 140. Thermal block 110 can be made from materials that exhibit good thermal properties. Below the thermal block and thermally coupled to the thermal block can be thermoelectric devices (not shown). Thermoelectric devices are solid-state devices that utilize the Peltier effect to pump heat from one side to another in response to a current or voltage applied to electrical leads attached to the devices. Thermoelectric devices can be used for both heating and cooling a sample block while occupying a relatively small space.

The thermoelectric devices can be electrically connected to interface board 120 with, for example, solder. Interface board 120 can provide various additional levels of functionality to the instrument. The interface board can also include, for example, connections for thermal sensors, analog-to-digital converters, digital-to-analog converters, memory devices, as well as contribute to solutions for hermetically sealing the thermoelectric device.

The interface board can additionally be connected to amplifier board 130 and main controller board 140. Amplifier board 130 determines the voltage or current required for heating and cooling the sample block with the thermoelectric devices by executing computer readable instructions and algorithms. Amplifier board can also be connected to the main controller board 140. Connections to the main controller board 140 can provide the main controller with thermal sensor readings, digital data from analog-to-digital converters, memory data and provide digital-to-analog converters to the main controller. All of the functions listed can be utilized by the main controller to control the current or voltage to the thermoelectric devices thereby enabling precise temperature control for the sample block and biological samples. Main controller board 140 can also provide various communication interfaces. Examples of these interfaces are RS232, RS422, RS485, CAN, Ethernet, Bluetooth, IEE-488, wireless, USB and Firewire. Main controller board 140 can further provide connections for user interfaces such as eGUI, touch screen, printer, mouse and keyboard as well as data storage devices.

Figure 2:
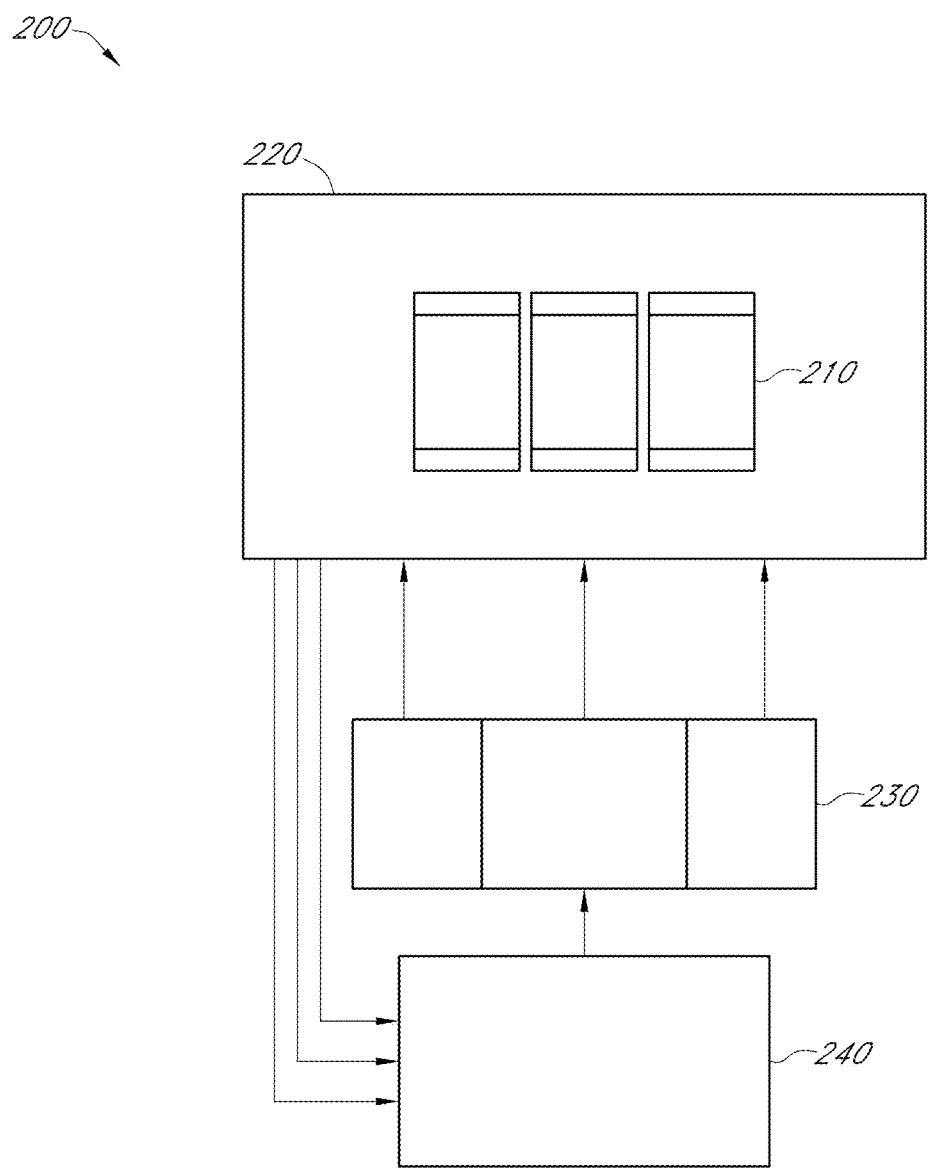
FIG. 2 is a block diagram that illustrates a multi-channel power amplifier system layout used to control the temperature of a sample block assembly, according to the prior art.

A variation on the prior art of FIG. 1 is depicted in FIG. 2. FIG. 2 also is representative of the prior art. Instrument 200 includes thermal block 210, Interface Board 220, Amplifier Board 230 and main processor board 240. In this case thermal block 210 is divided into 3 equal sized segments thermally isolated from each other. Each segment is associated with a dedicated thermoelectric device (not shown) directly underneath. Each thermoelectric device is controlled by one of three independent amplifier channels 230a-230c located on amplifier board 230. This architecture enables independent control of each thermoelectric device. While instrument 200 provides greater flexibility to a user, the addition of two additional amplifier channels and two additional block segments can increase the dimensions of both interface board 220 and amplifier board 230 as well as the overall complexity of the instrument. Greater PCB dimensions can also contribute to a physically larger instrument that may be difficult for some laboratories to accommodate.

Figure 3:
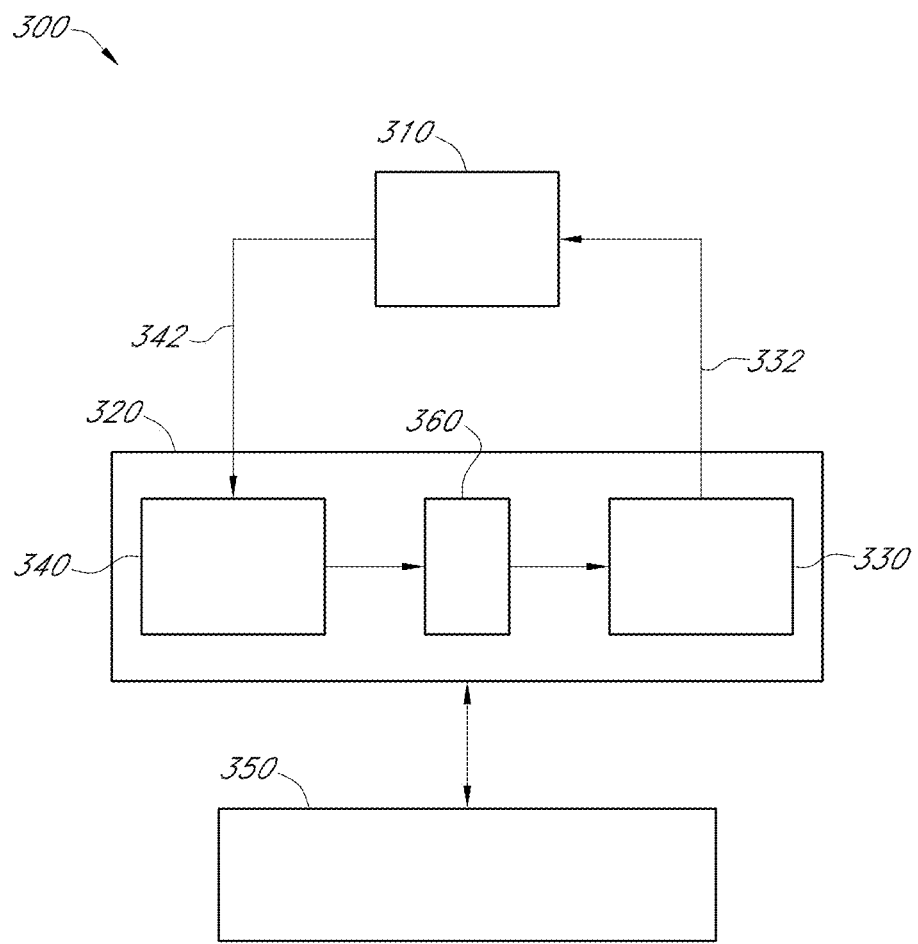
FIG. 3 is a block diagram that illustrates a power amplifier system layout used to control the temperature of a sample block assembly, in accordance with various embodiments.

A first embodiment shown in FIG. 3 is a distinct improvement to the prior art architectures depicted in FIG. 1 and FIG. 2. Instrument 300 includes thermal block 310, thermal control unit 320 and main controller 350. Thermal block 310 can have a first surface configured for receiving a sample support device. In some embodiments the thermal blocks can be a thermally conductive metal. In some embodiments the metal can be, but not limited to, aluminum, copper, silver or gold. In some embodiments the sample block can be a ceramic, such as, silicon carbide. The sample support device can be any sample support device known in the art, such as microtiter plates, individual tubes, tube strips, glass, metal or plastic slides or any other support device compatible with biological analysis. Each sample support device can contain any number of locations to support numerous samples. The number of sample locations can be from 1 sample to thousands of sample locations. For example, sample support devices can accommodate 1, 4, 8, 12, 16, 24, 32, 48, 96, 384, 1536, 2048, 3072 or any other number of samples required for biological analysis. Each sample location can be circular or rectangular. Each sample location can further contain a flat bottom, a concave bottom, a conical bottom or no bottom. Each sample location can further be sized to contain various sample volumes. Sample volumes can be from, for example, 5 picoliters up to 100 microliters, but not limited to this range. Each sample support device can further be of various geometries such as rectangular or round, but not limited to these geometries.

Thermal block 310 can further have a second surface opposite the first surface. The second surface can be thermally coupled to one or more thermoelectric devices (not shown). Each thermoelectric device can include one or more electrical leads. The thermal coupling can include an interface material. Interface materials are well known in the art and can be, for example, thermal grease, graphite sheets or paste, phase change coated foil, pads infused with aluminum or silicon oxide or any number of available thermal adhesives. Interface materials can further provide compliance between the sample block and the thermoelectric device to ensure uniform thermal contact between the thermal block and the thermoelectric device.

Thermal block 310 can also be thermally coupled to one or more thermal sensors (not shown). Thermal sensors are well known in the art, and are available in various shapes and sizes. Thermal sensors can be, for example, resistance temperature devices (RTD), thermistors, thermocouples, infrared (IR) detectors or silicon bandgap devices. The thermal sensor can be coupled to a surface of the sample block or embedded into the sample block. The thermal sensor can be coupled by thermal adhesive, mechanical clips or springs, thermal grease or any other thermal interface known in the art.

Thermal control unit 320 can include an electrical power supply section 330 and an interface section 340. The combination of electrical power supply section 330 and interface section 340 into thermal control unit 320 eliminates the need for two PCBs as practiced by the prior art. The electrical power supply section 330 can be primarily a voltage source or current source. The electrical power supply section can further be adjustable to provide various amounts of voltage or current to the thermoelectric devices. The electrical power supply section can further be connected to the one or more electrical leads of the thermoelectric devices through electrical control interface 332.

Thermal control unit 320 can further include an interface section 340. Interface section 340 can provide various functions. The various functions can include the functions previously described regarding interface board 120 of FIG. 1. In some embodiments the interface can provide, for example, persistent memory, volatile memory, analog-to-digital data conversion, digital-to-analog data conversion and communications. In some embodiments thermal control unit 320 can include a processor 360. In some embodiments interface section 340 can include the processor. In some embodiments electrical power supply section 330 can include the processor. In some embodiments interface section 340 and power supply section 330 can each include a processor.

Processor 360 can provide thermal control to the sample block. In some embodiments interface 340 can be connected to one or more thermal sensors (not shown) coupled to the thermal block through sensor interface 342 to enable closed-loop thermal control. In some embodiments the closed-loop thermal control can include proportional, integral and derivative elements (PID). In some embodiments the closed-loop thermal control can include only one or two of the proportional, integral and derivative elements.

Processor 360 on thermal control unit 320 can further provide communications capabilities to instrument 300. In some embodiments the communications can be between interface section 340 and electrical power supply section 330. In some embodiments the communications can be between interface section 340 and main controller 350. In some embodiments the communications can be between the interface section 340 and the thermal sensors (not shown). In other embodiments the communications can be between interface section 340, main controller 350, electrical power supply section 330 and thermal sensors. In some embodiments communications can be uni-directional. In some embodiments communications can be bi-directional. In some embodiments communications can be a combination of uni-directional and bi-directional. In some embodiments the communications can include a standard protocol. The standard protocol can be, for example RS232, RS422, IEEE 488, CAN, Ethernet, Bluetooth, Firewire or any other protocol known in the art.

Further referring to FIG. 3, instrument 300 can also include main controller 350. Main controller 350 can also include a processor (not shown). The processor of main controller 350 can be separate and in addition to the processor included on thermal control unit 320. The processor of main controller 350 can provide instrument functions that are separate from and compatible with the processor of thermal control unit 320. In some embodiments the processor of main controller 350 can be connected to and in communications with the processor of thermal control unit 320. In some embodiments communications can be uni-directional. In some embodiments communications can be bi-directional. In some embodiments communications can be a combination of uni-directional and bi-directional. In some embodiments the communications can include a standard protocol. The standard protocol can be, for example RS232, RS422, IEEE 488, CAN, Ethernet, USB, Bluetooth, Firewire or any other protocol known in the art.

In the simplest embodiment main controller 350 can include an interface to the environment external to instrument 300. In one embodiment main controller 350 provides interaction with a user. The user can enter information into instrument 300 through an input device. Examples of input devices include, but are not limited to, touch screens, pointing devices such as a mouse, an external keyboard, one or more external computers and a keypad integrated into instrument 300. A user can also retrieve information from instrument 300. Information can be retrieved from instrument 300 by output devices that include, but are not limited to, embedded displays, printers, jump drives, one or more external computers, external hard drives and a Cloud interface. Input devices can communicate with and be connected to instrument 300 by various protocols and can be uni-directional or bi-directional. In some embodiments the communications can include a standard protocol. The standard protocol can be, for example RS232, RS422, IEEE 488, CAN, Ethernet, USB, Bluetooth, Firewire or any other protocol known in the art.

In another embodiment main controller 350 can communicate with thermal control unit 320. Communication with thermal control unit 320 can enable a user to input control parameters to instrument 300. The user can use control parameters to create a protocol for the instrument. The protocol can include thermal parameters and optical detection parameters. Control parameters can include, but are not limited to, setpoint temperatures, hold times or dwell times, thermal ramp rates, auto increment/decrement of time, auto increment/decrement of temperature, incubation temperature, number of temperature cycles, data collection portion of the protocol, number of optical filters and optical integration times.

In addition to creating a protocol as described above, a user can also retrieve information from the instrument. Information can be retrieved through any of the output devices described above. A user can retrieve information, such as, status of the instrument. In some embodiments the status can include the availability of the instrument. In another embodiment the retrieved information can include the run status of the instrument. The run status can include, but not be limited to, the name of the protocol being run, the current temperature, the cycle number being run, the finish time of the protocol and errors during the run.

It should be noted that thermal control unit 320 differs from the prior art in that thermal control unit 320, and therefore the interface system 340, is separated from the thermoelectric device. Locating thermal control unit 320 away from the thermoelectric device can allow the thermal block 310 and thermoelectric devices to occupy a smaller geometry than the prior art. Separating thermal control unit 320 from the thermoelectric device can also enable a scalability opportunity. In some embodiments thermal block 310 may be configured in multiple block segments. Each block segment can include a thermoelectric device and a thermal sensor. An instrument, therefore, can be constructed of more than one block segment with each block segment correlated to a dedicated thermal control unit. Such an instrument is shown in FIG. 4.

Instrument 400 includes three block segments 410a-410c. Each block segment can include any number of sample locations. Each sample location can be capable of containing a sample volume. Each of block segments 410a-410c can also be thermally coupled to a temperature sensor and a thermoelectric device similar to instrument 300 of FIG. 3. Instrument 400 can also include thermal control units 420a-420c. Each thermal control unit 420a-420c can also include a processor (not shown), an interface section (not shown) and an electrical power supply section (not shown) similar to thermal control unit 320 of FIG. 3. Each thermal control unit 420a-420c can be associated with a single block segment. The correlation of one block segment to one thermal control unit can allow thermal control of each block segment independent of another. The independent control of the block segments can provide increased flexibility to the user. This flexibility can include running all block segments with the same protocol as well as being capable of running a different protocol in each segment. Instrument 400 further includes main controller 450. The increased flexibility can also be realized by locating thermal control units 420a-420c away from the thermoelectric devices. The increased flexibility can also be realized by locating thermal control units 420a-420c in a different plane than the thermoelectric devices. The increased flexibility can further be realized when adding additional block segments to the instrument. Additional block segments can be realized by including an additional thermal control unit thereby precluding the re-design of an interface board such as presented in the prior art of FIG. 1. Main controller 450 can include any or all of the functionality presented above for main controller 350 of FIG. 3, main controller 240 of FIG. 2 and main controller 140 of FIG. 1. One skilled in the art will realize that the depiction of three block segments and three thermal control units is not limiting and that any number of segments can be included.

An additional advantage of correlating one block segment to one thermal control unit is that an instrument can be modularized. For example, a block segment capable of containing 16 samples coupled to a thermal control unit can be the foundation for a family of instruments by adding additional block segments and their corresponding thermal block units. By utilizing a common architecture of 16 samples, for example, with a thermal control unit can reduce cost and permit easy upscaling and downsizing to meet customer needs.

Figure 4:
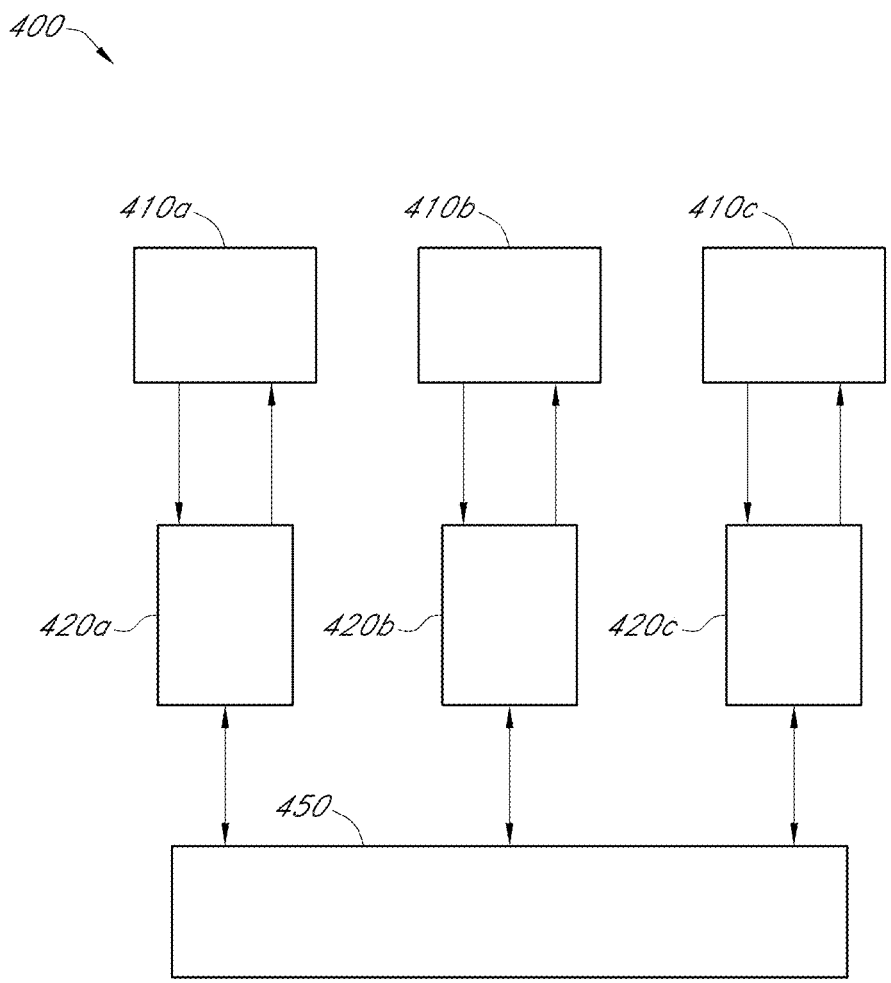
FIG. 4 is a block diagram that illustrates a multi-module power amplifier system layout used to control the temperature of a sample block assembly, in accordance with various embodiments.

In some embodiments block segments 410a-410c of FIG. 4 can be adjacent to each other such that a standard microtiter plate can be accommodated across all segments. As presented previously, standard microtiter plates are known in the art, and can include, for instance, 24 wells, 48 wells, 96 wells and 384 wells. In another embodiment block segments 41a-410c can be separated from each other to prevent the use of a standard microtiter plate from being accommodated across all segments. In such an embodiment, each block segment can be considered to be thermally independent.

Locating thermal control unit 320 of FIG. 3 and thermal control units 420a-420c of FIG. 4 away from the thermoelectric device can also present a challenge to isolate the thermoelectric device from the ambient conditions. It is known in the art that thermoelectric devices are sensitive to moisture. The moisture can be, for example, from water vapor. Ambient conditions with high humidity can provide the water vapor. Exposure to moisture can result in a degradation of the thermoelectric device resulting in early failure.

Figure 5:
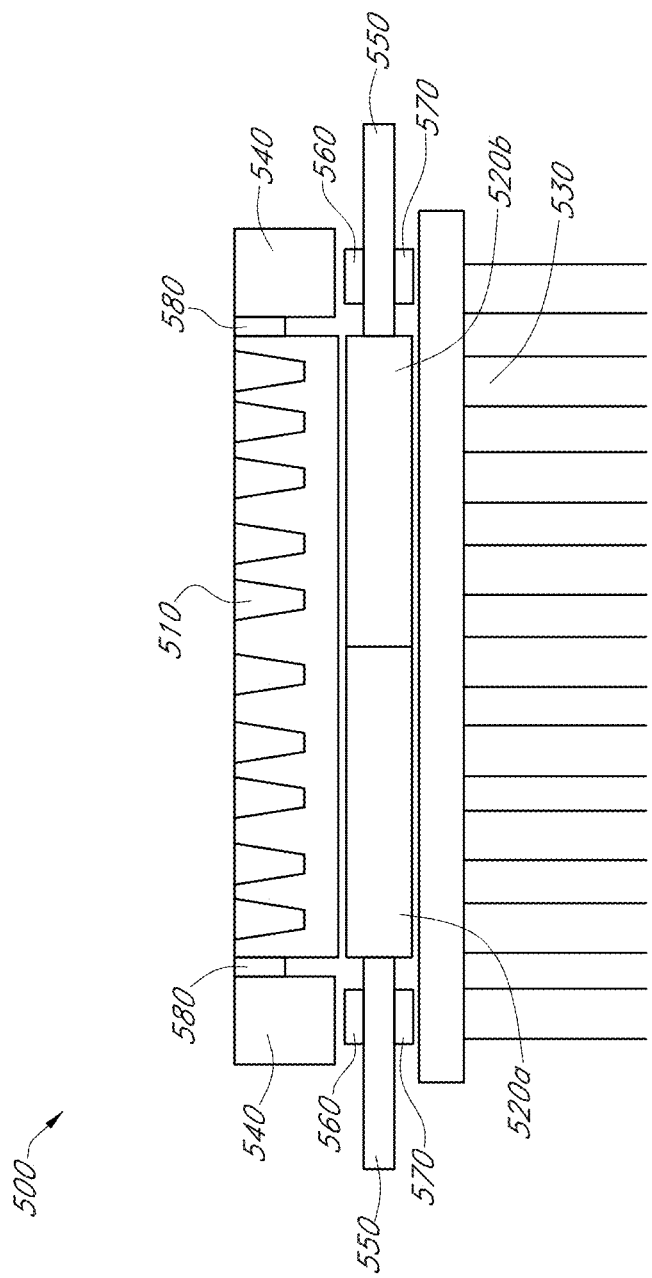
FIG. 5 is a block diagram that illustrates a sealing technique according to the prior art.

FIG. 5 is a block diagram of an instrument of the prior art. FIG. 5 depicts a technique for sealing the thermoelectric devices from ambient moisture. Instrument 500 includes thermoelectric devices 520a and 520b located between sample block 510 and heat sink 530. Heat sink 530 can provide a thermal path for removal of excess heat from the thermal block particularly during cooling of the thermal block. Heat sink 530 can be thermally coupled to thermoelectric devices 520*a* and 520*b* with a thermally conductive, compliant layer (not shown) as previously described. Thermoelectric devices can also be thermally coupled to thermal block 310 with a similar technique.

Instrument 500 further includes an interface board 550. Interface board 550 can provide the electrical connections necessary between thermoelectric devices 520*a* and 520*b* and an electrical power source. The electrical power source is known in the prior art as an amplifier and is shown in FIG. 1 as reference 130. Instrument 500 further includes a drip pan 540. Drip pan 540 can be positioned around the perimeter of thermal block 510. Drip pan 540 can be constructed of a thermally insulating material to isolate thermal block 510 from components that may be at a lower temperature than the temperature of thermal block 510. The lower temperature can be ambient temperature. The thermal isolation can be advantageous to prevent heat from thermal block 510 from conducting out of thermal block 510 which can result in the edges of thermal block 510 being cooler than the middle region of thermal block 510. Drip pan 540 can also accommodate fasteners (not shown) to assist in sealing the thermoelectric devices 520*a* and 520*b* from ambient as will be discussed below.

Isolating the thermoelectric devices 520*a* and 520*b* from exposure to moisture can be accomplished with a hermetic seal. The hermetic seal diagrammed in FIG. 5 can be accomplished with components 560, 570 and 580. As shown in FIG. 5 moisture can come in contact with thermoelectric devices 520*a* and 520*b* through gaps between thermal block 510 and drip pan 540, between drip pan 540 and interface board 550 and between interface board 550 and heat sink 530.

In the prior art, sealing element 560 can be an adhesive backed foam based material located on the upper surface of interface board 550. Sealing element 560 can be a dye cut element. Sealing element 560 can further be shaped in a generally rectangular shape and define the perimeter of the thermoelectric devices 520*a* and 520*b*. Sealing element 560 can further provide compliance to compensate for irregularities in the bottom surface of drip pan 540 and the top surface of interface board 550. Sealing element 560 can act to prevent moisture from reaching thermoelectric coolers 520*a* and 520*b* through the gap between drip pan 540 and interface board 550.

In the prior art, sealing element 570 can be constructed similar to sealing element 560 and located opposite sealing element 560 on the bottom surface of interface board 550. Sealing element 570 can further provide compliance to compensate for irregularities in the bottom surface of interface board 550 and the top surface of heat sink 530. Sealing element 570 can act to prevent moisture from reaching thermoelectric coolers 520*a* and 520*b* through the gap between interface board 550 and heat sink 530.

In the prior art, sealing element 580 can be incorporated to prevent thermoelectric devices 520*a* and 520*b* from being exposed to moisture through the gap between drip pan 540 and thermal block 510. In the prior art, sealing element 580 can serve two functions. One function can be preventing moisture from coming in contact with thermoelectric devices 520*a* and 520*b*. A second function can be to prevent heat from thermal block 510 from conducting away from thermal block 510 and reaching drip pan 540. Because of the additional functionality, sealing element 580 in the prior art is constructed of a different material than sealing elements 560 and 570. In the prior art sealing element can be constructed of materials such as silicone rubber.

Although not shown in FIG. 5, instruments of the prior art can include complementary features on drip pan 540 and thermal block 510 between which sealing element 580 can be located. Also present in the prior art and not shown in FIG. 5 are fasteners which can secure drip pan 540 to heat sink 530 thereby compressing sealing elements 560, 570 and 580 to seal thermoelectric elements 520*a* and 520*b* from moisture.

Referring now to FIG. 3 and the previous discussion of FIG. 3, the functionality of the interface board of the prior art has been moved away from thermal block 310 and its associated thermoelectric device. As such, hermetically sealing a thermoelectric device from ambient moisture conditions cannot be accomplished as discussed in the prior art.

Figure 6A:
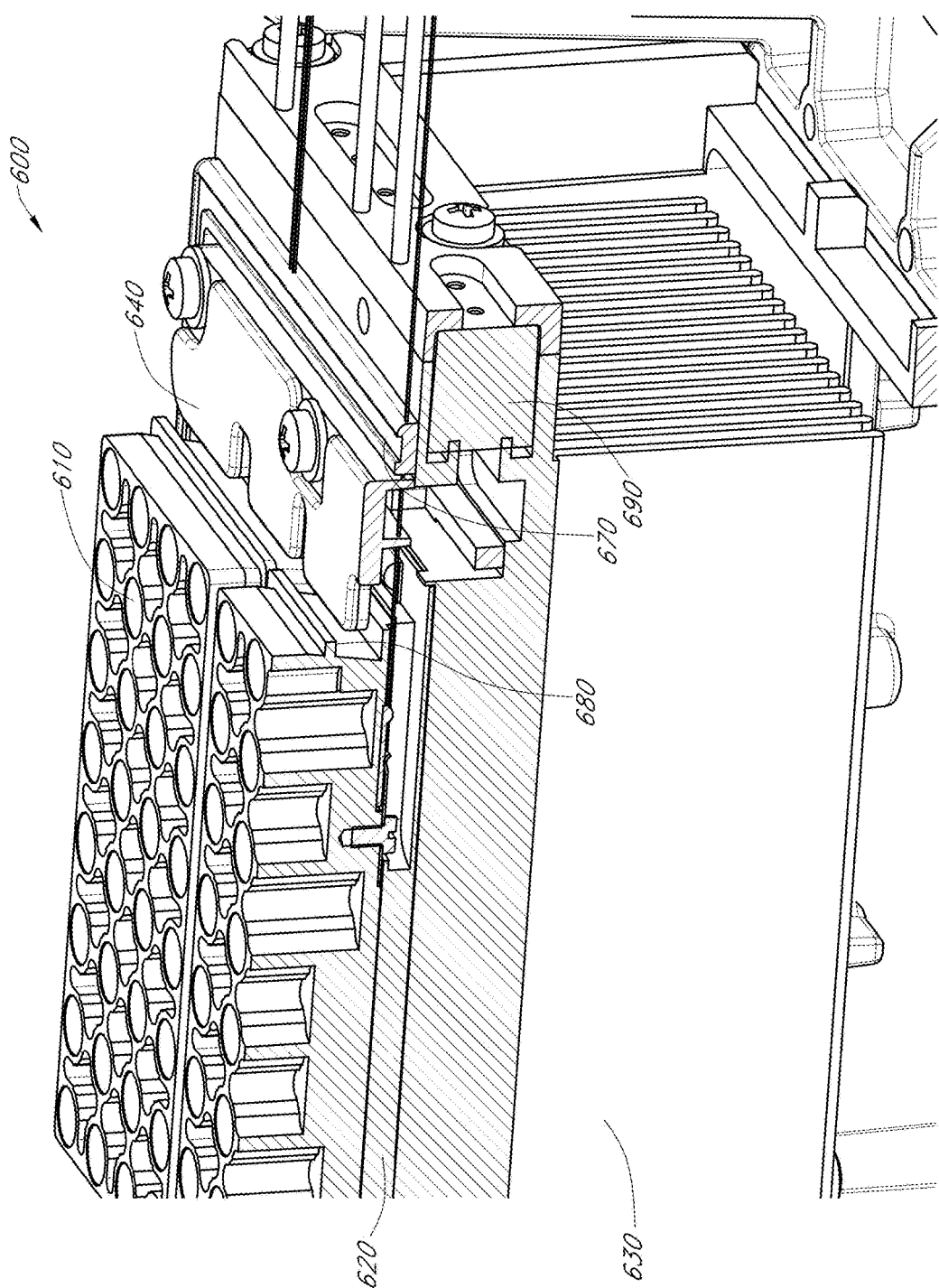
FIGS. 6A-6C is a block diagram that shows a sealing techniques, in accordance with various embodiments.
Figure 6B:
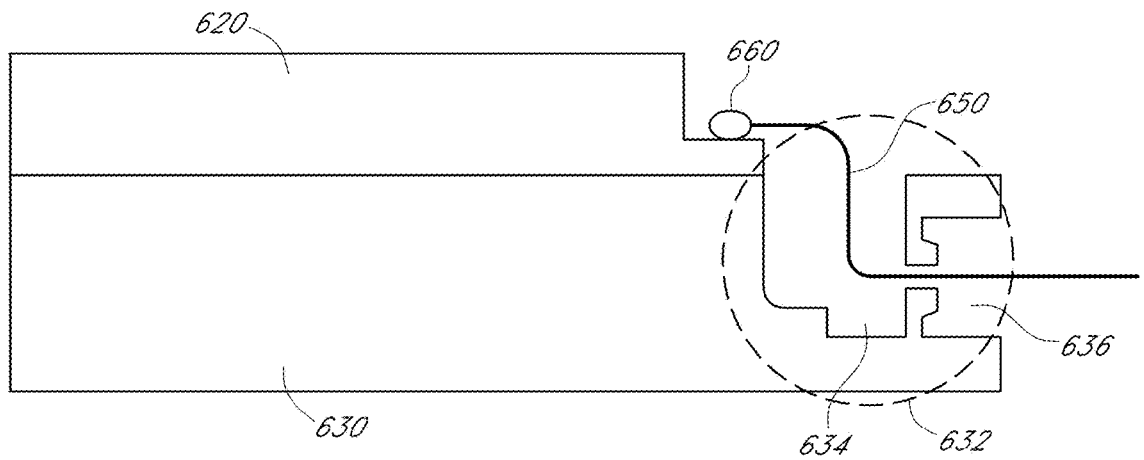

FIGS. 6A and 6B are block diagrams of an improved technique for hermetically sealing thermoelectric devices in instrument 600. Instrument 600 can include heat sink 630, thermal block 610 and drip pan 640. Drip pan 640 can be configured to surround the upper perimeter of thermal block 610. Drip pan 640 can further be configured to accommodate fasteners to secure drip pan 640 to heat sink 630. Thermoelectric devices 620 are located between thermal block 610 and heat sink 630. As previously discussed, it is well known in the art that thermoelectric devices are negatively affected by exposure to moisture. Moisture can cause corrosion of thermoelectric devices, resulting in areas of increased electrical resistance. The increased electrical resistance together with the electrical current flowing through the device can cause hot spots on the devices which eventually can cause physical failure. It is important therefore to minimize contact of thermoelectric devices with moisture particularly during operation.

As shown in FIG. 6A and FIG. 6B, thermoelectric devices 620 are located within a space bounded by thermal block 610, heat sink 630 and drip pan 640. It is important therefore that this space be isolated from ambient conditions. As shown in FIG. 6B, thermoelectric device 620 can include one or more electrical leads 650. Electrical leads 650 can be electrical conduits between thermoelectric device 620 and a thermal control unit (not shown). A representative thermal control unit is shown in FIG. 3 reference 320.

To isolate thermoelectric device 620, therefore, attention is drawn to three areas of FIG. 6A and FIG. 6B. First an air gap can exist between drip pan 640 and the upper perimeter of thermal block 610. Second an air gap can exist between drip pan 640 and heat sink 630. Lastly, connecting electrical leads 650 to a thermal control unit can result in a gap around electrical leads 650.

Referring to FIG. 6A, a first gap can be seen between an upper surface of heat sink 630 and the bottom surface of drip pan 640. It can be desirable to provide a first seal 670 to close the first gap. During the operation of instrument thermal block 610 can be subjected to frequent changes in temperature above ambient. In contrast heat sink 630 and drip pan 640 are known to exhibit better thermal stability and maintain a temperature closer to ambient. Further, the upper surface of heat sink 630 and the bottom surface of drip pan 640 are known to be distanced away from thermal block 610 so as not have a negative effect on the temperature of thermal block 610. Materials suitable for filling an air gap between heat sink 630 and drip pan 640 should have properties that are not only compliant but should also be air tight. In one embodiment a foam based gasket material can be suitable as a second seal to hermetically seal the second gap between the upper surface of heat sink 630 and the lower surface of drip pan 640. For convenience it can also be desirable for the foam based gasket material to be adhesive backed on one or both sides. It is noted that the suggestion of an adhesive backed foam based gasket in this embodiment should not be considered limiting. One skilled in the art will understand that any material exhibiting the desirable properties would be an appropriate material.

Referring again to FIG. 6A, a second gap can be seen between the upper perimeter of thermal block 610 and the bottom surface of drip pan 640. It can be desirable to provide a second seal 680 to close the second gap. During the operation of instrument thermal block 610 can be subjected to frequent changes in temperature. Thermal block 610 can expand and contract in response to temperature changes. Expansion and contraction of thermal block 610 can cause difficulty in firmly securing drip pan 640 to thermal block 610. Further, drip pan 640 can be thermally stable at ambient conditions and cause a temperature gradient between thermal block 610 and drip pan 640. A temperature gradient in this area can result in the edges of the thermal block becoming cooler than the center of the thermal block as heat conducts from thermal block 610 to drip pan 640. Materials suitable for filling an air gap between thermal block 610 and drip pan 640 should have properties that are not only compliant and air tight but should also be thermally resistive. In one embodiment a polymer such as silicone rubber can be used as second seal 680 to hermetically seal the second gap between the upper perimeter of thermal block 610 and lower surface of drip pan 640. It is noted however, that the suggestion of silicone rubber as second seal 680 in this embodiment should not be considered limiting. One skilled in the art will understand that any material exhibiting the desirable properties would be an appropriate material.

Figure 6C:
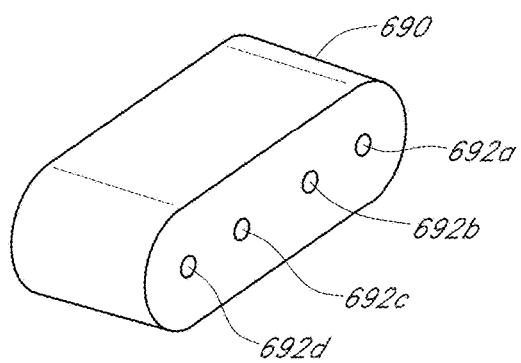

As previously described, instrument 600 has similarities to instrument 300 shown in FIG. 3, and differs from the prior art of FIG. 1 in that the interface board functionality of the prior art is located away from the thermal block and associated thermoelectric module. The absence of an interface board in FIG. 6 presents a challenge for ensuring an hermetic seal around the connection between electrical leads 650 of thermoelectric device 620 and a thermal control unit. It is well known in the art that a heat sink is a component of an instrument such as shown in FIG. 6A and FIG. 6B. However, one skilled in the art may note that heat sink 630 depicted in FIG. 6B may not be a recognizable geometry in the prior art. In particular, region 632 of FIG. 6B can differentiate heat sink 630 from the prior art.

Region 632 of FIG. 6B includes cavity 634, and defined opening 636. Cavity 634 can be included to provide a space for electrical leads 650 to be inserted into defined opening 636. As shown in region 632 defined opening 636 can be substantially larger than the dimensions of electrical leads 650. As such a third seal 690 can be located in defined opening 636 to fill the portion of defined opening 636 not occupied by electrical leads 650. Third seal 690 can be constructed such that third seal 690 is slightly larger than defined opening 636. Materials suitable for filling defined opening 636 can have properties that are compliant thereby providing an air tight fit against an inner surface of defined opening 636. In some embodiments third seal 690 can be made from silicone rubber. In another embodiment third seal 690 can be made from a compliant adhesive. It is noted however, that the suggestions of silicone rubber and adhesive as suitable materials for third seal 690 in these embodiments should not be considered limiting. One skilled in the art will understand that any material exhibiting the desirable properties would be an appropriate material.

Third seal 690 includes channels 692a-692d. Channels 692a-692d of third seal 690 can accommodate electrical leads 650 as well as thermal sensor leads (not shown). In one embodiment channels 692a-692d can have an internal diameter dimensioned slightly smaller than the outside diameter of electrical leads 650 and the outside diameter of thermal sensor leads (not shown). Such dimensioning can provide an interference fit that can provide an hermetic seal around electrical leads 650 and thermal sensor leads (not shown). In another embodiment channels 692a-692d can have an internal diameter that is slightly larger than the outside diameter of electrical leads 650 and the outside diameter of thermal sensor leads (not shown). While such dimensioning can ease the insertion of electrical leads 650 and thermal sensor leads (not shown) an air gap can result around the electrical leads. The air gap resulting from a slightly larger outside diameter of channels 692a-692d can be filled with a material suitable for providing an hermetic fit around electrical leads 650 and thermal sensor leads (not shown). In some embodiments the air gap around electrical leads 650 and the thermal sensor leads (not shown) can be filled with a compliant adhesive. In another embodiment the air gap around electrical leads 650 and the thermal sensor leads (not shown) can be filled with thermal grease. It is noted that the suggestions of a compliant adhesive and thermal grease as suitable materials to fill the air gap around electrical leads 650 and the thermal sensor leads in these embodiments should not be considered limiting. One skilled in the art will understand that any material exhibiting the desirable properties would be an appropriate material.

A fourth air gap can also exist. Each thermoelectric device 620 can include one or more electrical leads 650 as previously described. Electrical leads 650 are well known in the art and can include electrical wire. Electrical wire can include one or more electrical conductors surrounded by a layer of insulation. The insulation can include any material with properties that provide electrical insulation. Electrical insulation materials are well known in the art and can include, but not being limited to, plastic, rubber, Teflon and polypropylene. The insulation surrounding the one or more electrical conductors serves a purpose of isolating the one or more electrical conductors from other electrical conductors in close proximity to the electrical leads. The insulation however, does not provide an air tight channel from one end of the conductor to the other. Therefore an air gap can exist between the insulation and the one or more electrical conductors. This air gap can be sealed by a fourth seal 660. Fourth seal 660 can be any material that can be applied to the end of the one or more electrical leads attached to the thermoelectric device. A material such as a Room Temperature Vulcanizing silicone (RTV silicone) can be a suitable material that can be easily applied and distributed between each of the one or more electrical conductors and the insulation thereby forming an air tight seal.

Figure 7:
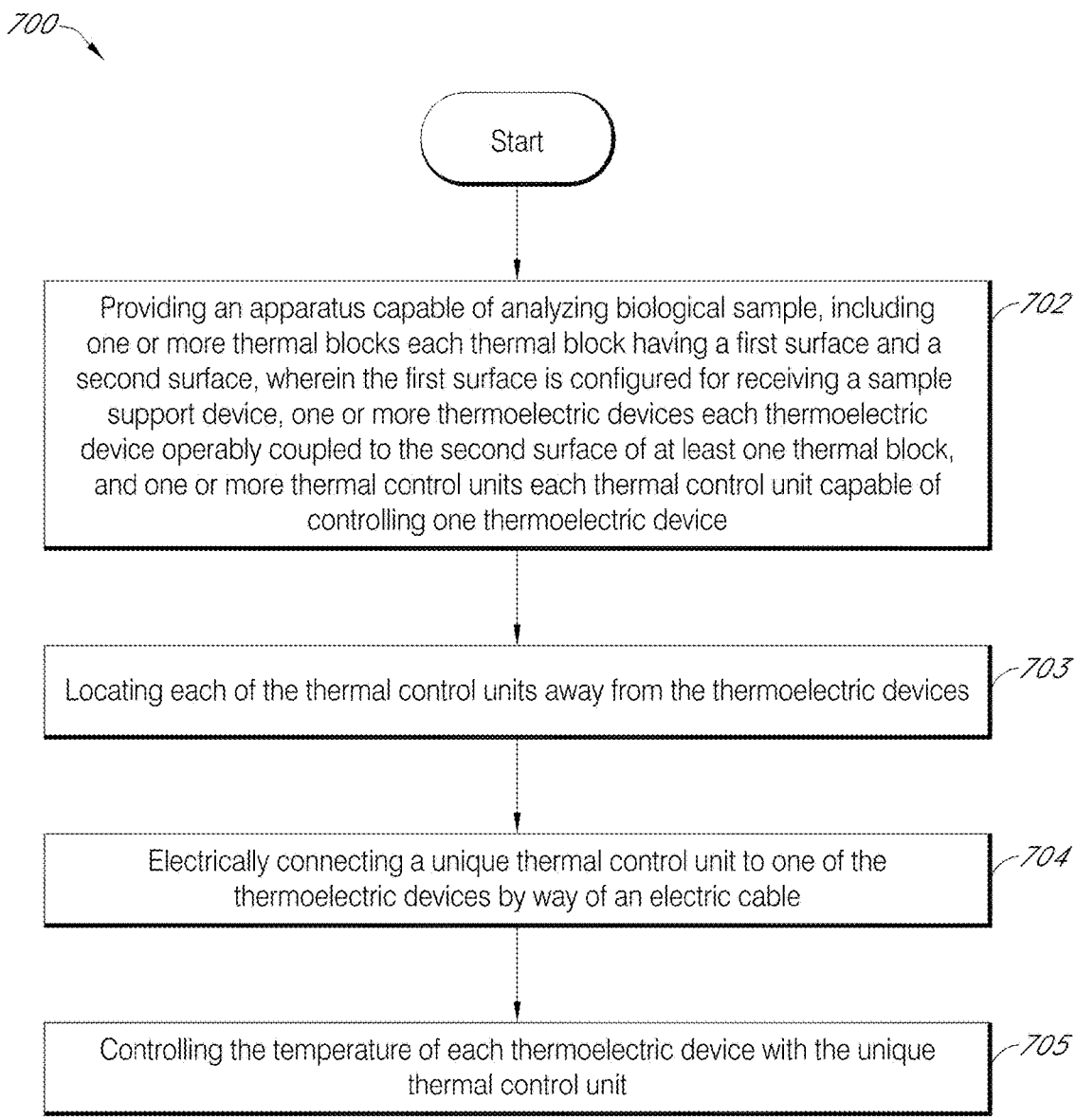
FIG. 7 is an exemplary process flowchart showing how multiple thermal control units can be utilized to control multiple thermoelectric devices, in accordance with various embodiments

FIG. 7 is an exemplary process flowchart showing how multiple thermal control units can be utilized to control multiple thermoelectric devices, in accordance with various embodiments. In step 702 an apparatus capable of analyzing biological sample is provided. In various embodiments, the apparatus can include one or more thermal blocks, one or more thermoelectric devices and one or more thermal control units. In various embodiments, each thermal block can include a first surface and a second surface. In various embodiments, the first surface can be configured to receive a sample support device. In various embodiments, each of the thermoelectric devices can be operably coupled to the second surface of a thermal block. In various embodiments, each of the thermal control units can be capable of controlling one thermoelectric device. In various embodiments, in step 703, each of the thermal control units can be located away from the thermoelectric devices.

In various embodiments, in step 704, the thermal control units can be located away from the thermoelectric devices by electrically connecting a unique thermal control unit to one of the thermoelectric devices by way of an electrical cable. In various embodiments the electrical cable can provide flexibility by enabling the location of each thermal control unit to be any distance required by the instrument. In various embodiments, the electrical cable can provide flexibility by enabling the location of each thermal control unit to be in any orientation with respect to the thermoelectric device. In various embodiments, the electrical cable can provide flexibility by enabling the location of each thermal control unit to be in any orientation and any distance with respect to the thermoelectric device.

In various embodiments, in step 705, the temperature of a thermoelectric device can be controlled by the unique thermal control unit. In various embodiments, controlling the temperature of a thermoelectric device with the unique thermal control unit can provide flexibility by enabling each thermoelectric device to be controlled to a different temperature for a different period of time by the thermal control unit attached by the electrical cable.

While the foregoing embodiments have been described in some detail for purposes of clarity and understanding, it will be clear to one skilled in the art from a reading of this disclosure that various changes in form and detail can be made without departing from the true scope of the embodiments disclosed herein. For example, all the techniques, apparatuses, systems and methods described above can be used in various combinations.

What is claimed is:

1. A thermal cycler system comprising:
   a sample block comprising a block first surface, an opposing block second surface, and a sample block perimeter, wherein the block first surface is configured for receiving a plurality of reaction vessels;
   a drip pan positioned along and outside the sample block perimeter;
   a thermoelectric device in thermal communication with the block second surface;
   a thermal sensor positioned to monitor temperature of the sample block;
   a thermal control unit comprising a computer processing unit and an electrical interface, the electrical interface being configured to electrically connect to the thermoelectric device by way of an electrical cable, wherein the thermal control unit is positioned outside the sample block perimeter;
   a heat sink comprising:
      a heat sink perimeter;
      a heat sink surface in thermal communication with the thermoelectric device; and
      a cavity positioned lateral to and outside of the sample block perimeter, the cavity recessed in the heat sink surface; and
      a sealing member positioned adjacent to the cavity between the cavity and the heat sink perimeter, the sealing member being configured to isolate at least the thermoelectric device from ambient moisture conditions,
   wherein the cavity and the sealing member are positioned to route the electrical cable from the thermoelectric device to the electrical interface.

2. The thermal cycler system of claim 1, wherein the sample block comprises a metal.

3. The thermal cycler system of claim 2, wherein the block first surface comprises depressions for receiving a sample support device.

4. The thermal cycler system of claim 2, wherein the block first surface is planar.

5. The thermal cycler system of claim 1, wherein the thermal control unit is positioned in a different plane than the thermoelectric device.

6. The thermal cycler system of claim 1, wherein the sealing member is a first sealing member and the system further comprises a second sealing member positioned to close a gap between the heat sink surface and the drip pan.

7. The thermal cycler system of claim 1, wherein the sealing member is a first sealing member and the system further comprises a second sealing member positioned to close a gap between the sample block perimeter and the drip pan.

8. The thermal cycler system of claim 1, wherein the electrical cable includes one or more electrical conductors, wherein the one or more electrical conductors have insulation, and wherein the sealing member is a first sealing member and the system further comprises a second sealing member positioned to close a gap between the one or more electrical conductors and the insulation.

9. The thermal cycler system of claim 1, wherein the sealing member is a first sealing member and the system further comprises second and third sealing members respectively positioned to close:
   (i) a first gap between the heat sink surface and the drip pan; and
   (ii) a second gap between the sample block perimeter and the drip pan.

10. The thermal cycler system of claim 1, wherein the sealing member is positioned within an opening of the heat sink adjacent the cavity, wherein the opening is positioned between the cavity and the heat sink perimeter to route the electrical cable from the thermoelectric device to the electrical interface.

11. The thermal cycler system of claim 1, wherein the sealing member comprises a channel configured to receive the electrical cable.

12. The thermal cycler system of claim 11, further comprising the electrical cable, wherein the electrical cable passes through the channel and extends across the cavity.

13. The thermal cycler system of claim 1, wherein the thermoelectric device is a first thermoelectric device, the thermal sensor is a first thermal sensor, the sample block comprises first and second block segments, and the system further comprises a second thermoelectric device and a second thermal sensor, the first and second thermoelectric devices are in thermal communication with the first and second block segments respectively, the first and second thermal sensors are positioned to monitor the first and second block segments respectively, the electrical interface is further configured to electrically connect to the second thermoelectric device, and the thermal control unit is configured to provide independent thermal control of the first and second block segments.

14. The thermal cycler system of claim 1, wherein the thermoelectric device is a first thermoelectric device, the thermal sensor is a first thermal sensor, the thermal control unit is a first thermal control unit, the sample block comprises first and second block segments, and the system further comprises a second thermoelectric device, a second thermal sensor, and a second thermal control unit, the first and second thermoelectric devices are in thermal communication with the first and second block segments respectively, the first and second thermal sensors are positioned to monitor the first and second block segments respectively, the first thermal control unit is configured to provide independent thermal control of the first block segment, and the second thermal control unit is configured to provide independent thermal control of the second block segment.

15. The thermal cycler system of claim 14, wherein the sample block comprises first, second, and third block segments, the system further comprising a third thermoelectric device, a third thermal sensor, and a third thermal control unit, the third thermoelectric device is in thermal communication with the third block segment, the third thermal sensor is positioned to monitor the third block segment, and the third thermal control unit is configured to provide independent thermal control of the third block segment.

16. A method for controlling a thermoelectric device in a thermal cycler system, the method comprising:
    providing a thermal cycler system, the thermal cycler system, comprising:
        a sample block comprising a sample block perimeter, a block first surface, and a second block surface, wherein the block first surface is configured for receiving a sample support device;
        a drip pan positioned along and outside the sample block perimeter;
        a thermoelectric device in thermal communication with the block second surface;
        a thermal sensor positioned to monitor temperature of the sample block;
        a thermal control unit positioned outside the sample block perimeter and electrically connected to the thermoelectric device by way of an electrical cable;
        a heat sink comprising:
            a heat sink perimeter;
            a heat sink surface in thermal communication with the thermoelectric device; and
            a cavity recessed in the heat sink surface at a location lateral to and outside the sample block perimeter; and
        a sealing member positioned adjacent to the cavity between the cavity and the heat sink perimeter, the sealing member being configured to isolate the thermoelectric device from ambient moisture conditions, wherein the cavity and the sealing member are positioned to route the electrical cable from the thermal control unit to the thermoelectric device; and
    controlling the temperature of the sample block by controlling the thermoelectric device.

17. The method of claim 16, wherein the sample block comprises a metal.

18. The method of claim 16, wherein the block first surface comprises depressions for receiving the sample support device.

19. The method of claim 16, wherein the thermal control unit is positioned in a different plane than the thermoelectric device.

20. The method of claim 16, wherein the sealing member is a first sealing member and the system further comprises a second sealing member positioned to close a gap between the heat sink surface and the drip pan.

21. The method of claim 16, wherein the sealing member is a first sealing member and the system further comprises a second sealing member positioned to close a gap between the sample block perimeter and the drip pan.

22. The method of claim 16, wherein the electrical cable includes one or more electrical conductors, wherein the one or more electrical conductors have insulation, and wherein the sealing member is a first sealing member and the system further comprises a second sealing member positioned to close a gap between the one or more electrical conductors and the insulation.

23. The method of claim 16, wherein the sealing member is a first sealing member and the system further comprises second and third sealing members respectively positioned to close:
    (i) a first gap between the heat sink surface and the drip pan; and
    (ii) a second gap between the sample block perimeter and the drip pan.

24. The method of claim 16, wherein the sealing member is positioned within an opening of the heat sink adjacent the cavity, wherein the opening is positioned between the cavity and the heat sink perimeter to route the electrical cable from the thermoelectric device to the thermal control unit.

25. The method of claim 16, wherein the sealing member comprises a channel configured to receive the electrical cable.

26. The method of claim 25, wherein the system further comprises the electrical cable, the electrical cable passing through the channel and extending across the cavity.

27. The method of claim 16, wherein the thermoelectric device is a first thermoelectric device, the thermal sensor is a first thermal sensor, the sample block comprises first and second block segments, and the system further comprises a second thermoelectric device and a second thermal sensor, the first and second thermoelectric devices are in thermal communication with the first and second block segments respectively, the first and second thermal sensors are positioned to monitor the first and second block segments respectively, and the thermal control unit is further configured to electrically connect to the second thermoelectric device and to provide independent thermal control of the first and second block segments.

28. The method of claim 16, wherein the thermoelectric device is a first thermoelectric device, the thermal sensor is a first thermal sensor, the thermal control unit is a first thermal control unit, the sample block comprises first and second block segments, and the system further comprises a second thermoelectric device, a second thermal sensor, and a second control unit, the first and second thermoelectric devices are in thermal communication with the first and second block segments respectively, the first and second thermal sensors are positioned to monitor the first and second block segments respectively, the first thermal control unit is configured to provide independent thermal control of the first block segment, and the second thermal control unit is configured to provide independent thermal control of the second block segment.

29. The method of claim 28, wherein the sample block comprises first, second, and third block segments, the system further comprising a third thermoelectric device, a third thermal sensor, and a third thermal control unit, the third thermoelectric device is in thermal communication with the third block segment, the third thermal sensor is positioned to monitor the third block segment, and the third thermal control unit is configured to provide independent thermal control of the third block segment.

* * * * *